(12) United States Patent
Nakagawa

(10) Patent No.: US 6,309,340 B1
(45) Date of Patent: Oct. 30, 2001

(54) MAGNET TYPE MEDICAL INSTRUMENT AND ELECTROMAGNET AND COIL USED IN IT

(75) Inventor: Kyoichi Nakagawa, Tokyo (JP)

(73) Assignee: Pulse Medical Co., Ltd. (JP)

( * ) Notice: Subject to any disclaimer, the term of this patent is extended or adjusted under 35 U.S.C. 154(b) by 0 days.

(21) Appl. No.: 09/242,241
(22) PCT Filed: Jul. 28, 1998
(86) PCT No.: PCT/JP98/03345
§ 371 Date: Feb. 10, 1999
§ 102(e) Date: Feb. 10, 1999
(87) PCT Pub. No.: WO00/06252
PCT Pub. Date: Feb. 10, 2000
(51) Int. Cl.[7] ................................................. A61N 1/00
(52) U.S. Cl. ................................................................ 600/14
(58) Field of Search ............................................ 600/9–15

(56) References Cited

U.S. PATENT DOCUMENTS 5,441,495 * 8/1995 Llboff et al. ........................... 600/13
5,518,495 * 5/1996 Kolt ....................................... 600/13
5,788,624 * 8/1998 Lu et al. ................................ 600/13

* cited by examiner

Primary Examiner—John P. Lacyk
(74) Attorney, Agent, or Firm—Bierman, Muserlian and Lucas

(57) ABSTRACT

The purpose of the present invention is to propose a magnet type medical instrument which can prevent the magnetic flux density from reducing remarkably even at a point distant from a magnetic pole of a core and realize a satisfactory pain-killing effect in a human body even at a point distant from the magnetic pole.

The electromagnet for the magnet type medical instrument comprises a first core 1 with first inner space and a first coil 3 which is wound round the first core 1 and which can generate a first magnetic field by applying an alternating current, a commutated current or a pulsating current to the first coil 3.

11 Claims, 18 Drawing Sheets

MAGNET TYPE MEDICAL INSTRUMENT AND ELECTROMAGNET AND COIL USED IN IT

TECHNICAL FIELD

The present invention relates to a magnet type medical instrument which can kill a pain in a human body by means of a magnetic field generated in it and an electromagnet and a coil used in it.

BACKGROUND ART

Generally speaking, an electromagnet used in a magnet type medical instrument which can kill a pain in a human body by means of a magnetic field generated in it comprises a core and a coil constituted by a metallic wire wound round the core and generates a magnetic field by applying an alternating current or a pulsating current to the coil.

The core of an electromagnet 30 used in a conventional magnet type medical instrument shown in FIG. 4 is constituted by sheets of silicon steel piled up so as to be shaped like a bar for example. As for this conventional type medical instrument, as soon as an alternating current is applied to the coil on condition that the electromagnet is put horizontally and magnetic powder 32 is put near a magnetic pole 31 of the core on a paper put horizontally, the powder distant from the magnetic pole is scattered rapidly while the powder near the magnetic pole is not so scattered as shown in FIG. 4. This means that the lines of magnetic force distant from the magnetic pole are scattered while those near the magnetic pole is not so scattered and that the magnetic flux density distant from the magnetic pole is low while that near the magnet pole is high. In case an alternating current was applied to the coil of the electromagnet 30 of the conventional type medical instrument on condition that the alternating voltage was 30V and the frequency was 50 Hz, the magnetic flux density 6 cm distant from a magnetic pole 31 of the core was 5% supposing the magnetic flux density at the magnetic pole 31 was 100%. Thus in this conventional type there is a problem that its pain-killing effect in a human body is small.

Thus, an object of the present invention is to propose an electromagnet and a coil for a magnet type medical instrument the pain-killing effect of which is large enough as it can keep high magnetic flux density even at any point distant from the magnetic pole of the core.

There is another problem in this conventional type that in case the electromagnet 30 shown in FIG. 4 generates a magnetic field in a human body the magnetic flux density is not constant at any part of the human body because the distance from the magnetic pole is not constant resulting in low magnetic flux density at parts distant from the magnetic pole.

Thus, another object of the present invention is to propose a magnet type medical instrument which can generate a magnetic field having a relatively uniform magnetic flux density in a human body.

There is furthermore another problem in this conventional type that in case the electromagnet 30 generates a magnetic field in a human body only an alternating current of 50 or 60 Hz in frequency is used to excite the coil for the electromagnet 30 although it is known that the effect of a frequency other than 50 or 60 Hz is better.

Thus, another object of the present invention is to propose a magnet type medical instrument in which an alternating current in an optimum frequency range can excite the coil for the electromagnet 30 in the medical instrument.

DISCLOSURE OF INVENTION

The magnet type medical instrument according to the present invention shown in FIG. 1, FIG. 2, FIG. 6 and FIG. 7 comprises a circular- or square-sectioned first core with a first inner space and a first coil which is wound round said first core and which can generate a first magnetic field by applying an alternating current, a commutated current or a pulsating current to said first coil.

Furthermore the magnet type medical instrument according to the present invention shown in FIG. 8 to FIG. 11 comprises a first core and a first coil as in the abovementioned embodiment and in addition a second coil which is wound in the first inner space of said first core so as to form a second inner space inside and which can generate a second magnetic field by applying an alternating current or a pulsating current to said second coil, said first coil and said second coil being wound in the same direction so that the polarity of said first magnetic field may coincide with that of said second magnetic field and the number of turns of said first coil and/or that of said second coil being regulated so that the phase of said first magnetic field may coincide with that of said second magnetic field.

Furthermore the magnet type medical instrument according to the present invention shown in FIG. 12 to FIG. 15 comprises a first core, a first coil, and a second coil as in the above-mentioned embodiment shown in FIG. 8 to FIG. 11 but said second coil is wound to its axis without forming said second inner space.

Furthermore the magnet type medical instrument according to the present invention shown in FIG. 16 to FIG. 19 comprises a first core, a first coil and a second coil as in the above-mentioned embodiment shown in FIG. 8 to FIG. 11 and in addition a second core which is arranged in said second inner space Furthermore the magnet type medical instrument according to the present invention shown in FIG. 24 and FIG. 25 comprises a first core, a first coil, a second coil and a disk-like yoke which is stuck on an end of each of said first core and said first and second coils to enclose them.

Furthermore the first core and the second core in the above-mentioned embodiments of the magnet type medical instrument according to the present invention are constituted by steel sheets wound in a shape like a circular- or square-sectioned sleeve.

Furthermore in a magnet type medical instrument according to the present invention, said first core and said second core can be replaced by a first non-magnetic bobbin and a second non-magnetic bobbin respectively.

Furthermore the magnet type medical instrument according to the present invention shown in FIG. 26 is characterized in that it comprises a transformer in which the primary voltage from an alternating current source to be applied to the primary winding is transformed into the secondary voltage at the secondary winding as an output voltage, a pair of electromagnets which can generate magnetic fields by applying said secondary voltage from said secondary winding to said electromagnets to kill a pain in a human body put between said electromagnets, a pair of supporting elements for supporting said pair of electromagnets for medical use, a fixing bed for sliding said pair of supporting elements so that said supporting elements may move close to or apart from each other resulting in making said electromagnets move close to or apart from said human body, and a pair of sliding terminals which are attached to said pair of supporting elements and which slide in contact with said secondary winding so as to regulate the number of turns of said secondary winding corresponding to the distance between said pair of electromagnets for medical use and a human body thereby to change said secondary voltage to be applied to said electromagnets.

Furthermore the magnet type medical instrument according to the present invention shown in FIG. 27 is characterized in that it comprises a transformer in which the primary voltage from an alternating current source to be applied to the primary winding is transformed into the secondary voltage at the secondary winding as an output voltage, a pair of electromagnets which can generate a magnetic field by applying said secondary voltage from said secondary winding to said electromagnets to kill a pain in a human body put between said electromagnets, a pair of distance sensors which are attached to said pair of electromagnets for medical use, which emit infrared rays against said human body and which can detect a distance between said pair of electromagnets and said human body by receiving said infrared rays reflected from said human body, a pair of supporting elements, a pair of sliding terminals which are attached to said pair of supporting elements and which slide in contact with said secondary winding so as to regulate the number of turns of said secondary winding thereby to change said secondary voltage to be applied to said electromagnets, a fixing bed for sliding said pair of supporting elements so that said supporting elements may move close to or apart from each other, and a control device having a driving mechanism for changing the distance between said pair of supporting elements so as to change the distance between said pair of sliding terminals corresponding to the input signal from said pair of distance sensors corresponding to the distance between said pair of electromagnets for medical use and said human body.

Furthermore the magnet type medical instrument according to the present invention shown in FIG. 28 comprises an electromagnet or a pair of electromagnets for medical use and a transformer for applying a transformed alternating current to said electromagnet for medical use and is characterized in that a frequency regulation device for regulating said transformed alternating current so that the frequency of said transformed alternating current may be 5 to 40 Hz is arranged between said electromagnet/electromagnets and said transformer.

According to an embodiment of the present invention shown in FIG. 1, FIG. 2, FIG. 6 and FIG. 7, the magnet type medical instrument has a first coil which is wound round a circular- or square-sectioned first core with a first inner space and which can generate a first magnetic field by applying an alternating current, a commutated current or a pulsating current to said first coil.

As the lines of magnetic force of the magnetic field do not intersect each other, the lines of magnetic force generated on said first inner space side of said first core are enclosed by those generated on the front or outer surface side of said first core. Thus, those generated on said inner space side go nearly straight in a long distance without scattering away from the axis of said first inner space. As shown in FIG. 3, in case said first coil in the magnet type medical instrument according to the present invention shown in FIG. 1 and FIG. 2 is put horizontally and magnetic powder 33 is put dispersively near a magnetic pole of the core on a white paper put horizontally, even if an alternating current is applied to said first coil, the powder 33 will not be diffused rapidly even at a point distant from the magnetic pole and the lines of magnetic force will be prevented from being diffused rapidly. As shown in FIG. 5, in case an alternating current with 30 V in voltage and 50 Hz in frequency is applied to the coil in the magnet type medical instrument according to the present invention, the magnetic flux density in a position 6 cm distant from the magnetic pole 31 of the core is reduced down to 31.0%, supposing that of the magnetic pole of the core is 100%. Thus, it is clarified that the magnetic flux density is prevented from being reduced at much less rate than that of the conventional type medical instrument shown in FIG. 4. It comes to the conclusion that the magnet type medical instrument according to the present invention can kill a pain in a human body satisfactorily as the magnetic flux density of the magnetic field even in a position distant from the magnetic pole of the core is not reduced so remarkably.

Furthermore, according to another embodiment of the present invention shown in FIG. 8 to FIG. 11, the magnet type medical instrument comprises a second coil which is wound in said first inner space of said first core so as to form a second inner space and which generate a second magnetic field by applying said alternating current or said pulsating current to said second coil. In addition, said first coil and said second coil are wound in the same direction and the number of turns of said first coil and that of said second coil are regulated so that the phase of the magnetic field of said first coil may coincide with that of said second coil. Thus, as the lines of magnetic force of said first magnetic field generated by said first coil enclose those of said second magnetic field generated by said second coil from outside so as to prevent it from diffusing, the latter can reach a position distant from a magnetic pole without diffusing. In the result, said magnetic type medical instrument can kill a pain in a human body satisfactorily because even the magnetic flux density distant from the magnetic pole of said first core is prevented from being reduced remarkably.

Furthermore, according to another embodiment of the present invention shown in FIG. 12 to FIG. 15, said second coil in said magnetic type medical instrument is wound to its axis without forming said second inner space in said first inner s pace, which is different from the above-mentioned embodiment shown in FIG. 8 to FIG. 11.

Thus, as the lines of magnetic force of said first magnetic field generated by said first coil enclose those of said second magnetic field in said first inner space generated by said second coil from outside so that they may be prevented from diffusing, the latter can reach a position distant from a magnetic pole without diffusing. In the result, said magnet type medical instrument can kill a pain in a human body satisfactorily because even the magnetic flux density distant from the magnetic pole of said first core is prevented from being reduced remarkably.

Furthermore, according to another embodiment of the present invention shown in FIG. 16 to FIG. 19, said magnet type medical instrument comprises a second core in its second inner space.

Thus, as the lines of magnetic force of said first magnetic field generated by said first coil enclose those of said second magnetic field in said first inner space generated by said second coil from outside so that it may be prevented from diffusing, the latter can reach a position distant from a magnetic pole without diffusing. In the result, said magnet type medical instrument can kill a pain in a human body satisfactorily because even the magnetic flux density distant from the magnetic pole of said first core is prevented from being reduced remarkably.

Furthermore, according to another embodiment of the present invention shown in FIG. 24 and FIG. 25, a disk-like yoke is stuck to an end of each of the core and the coil in the above-mentioned embodiments to enclose it.

Thus, as said end of each core generates little lines of magnetic force and the other end of each core generates the lines of magnetic force with the increased magnetic flux density, said magnetic type medical instrument can kill a pain in a human body satisfactorily.

Furthermore, said first core and said second core in the above-mentioned embodiments of the magnet type medical instrument according to the present invention can be constituted by steel sheets wound in a shape like a circular- or square-sectioned sleeve. Thus, said first core and said second core may be shaped in a shape like a circular- or square-sectioned sleeve optionally corresponding to the form of use.

Furthermore, the magnet type medical instrument according to the present invention shown in FIG. 26 comprises a pair of sliding terminals which are attached to a pair of supporting elements and which slide in contact with the secondary winding so as to regulate the number of turns of the second winding corresponding to the distance between a pair of the electromagnet for medical use and a human body to change the secondary voltage and to apply the magnetic field of an optimum magnetic flux density to the human body resulting in better pain-killing effect.

Furthermore, the magnet type medical instrument according to the present invention shown in FIG. 27 comprises a control device provided with a driving mechanism which can change the distance between a pair of supporting elements corresponding to the signal from a pair of distance sensors corresponding to the distance between the electromagnet for medical use and a human body thereby to apply a magnetic field of an optimum magnetic flux density to the human body, resulting in better pain-killing effect.

Furthermore, the magnetic type medical instrument according to the present invention shown in FIG. 28 comprises a frequency regulation device which can regulate the frequency of an alternating current transformed by a transformer so that it may be 5 to 40 Hz thereby to energize the electromagnet for medical use in an optimum frequency and which is put between the electromagnet for medical use and the transformer, resulting in better pain-killing effect.

BEST MODE FOR CARRYING OUT THE INVENTION

We explain the present invention further below based on the embodiments referring to said drawings.

Figure 1:
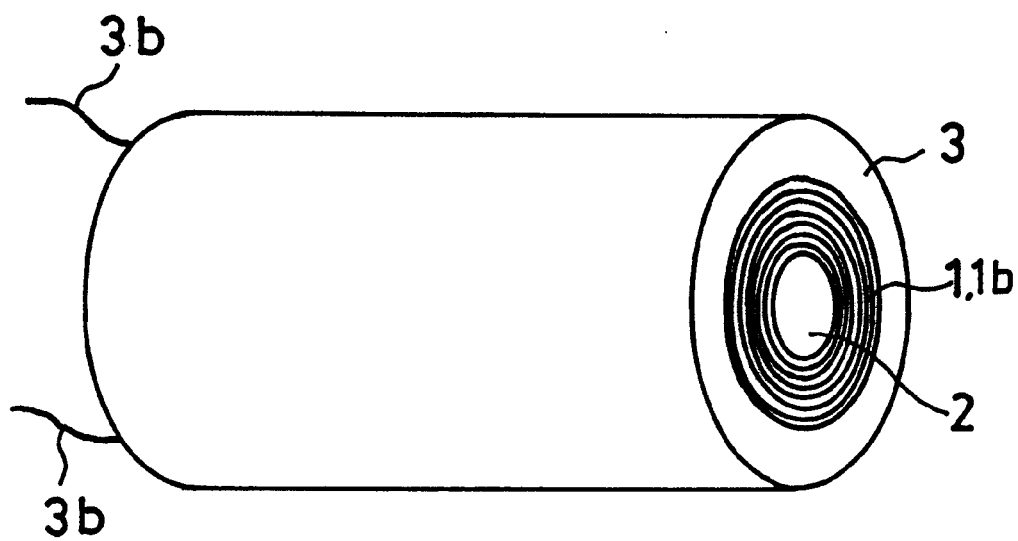
FIG. 1 shows a perspective view of an embodiment of an electromagnet and a coil in a magnet type medical instrument according to the present invention.
Figure 2:
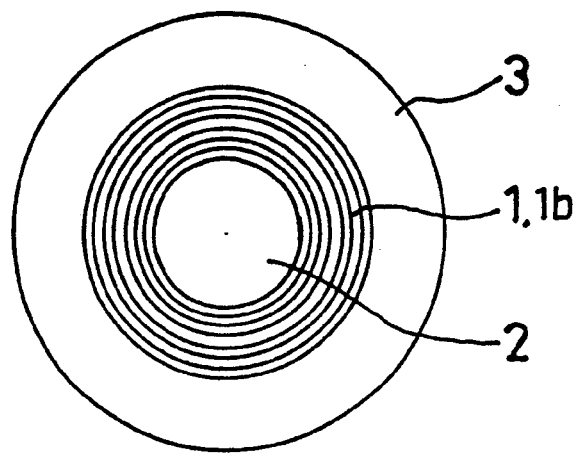
FIG. 2 shows a front view of the embodiment shown in FIG. 1.
Figure 4:
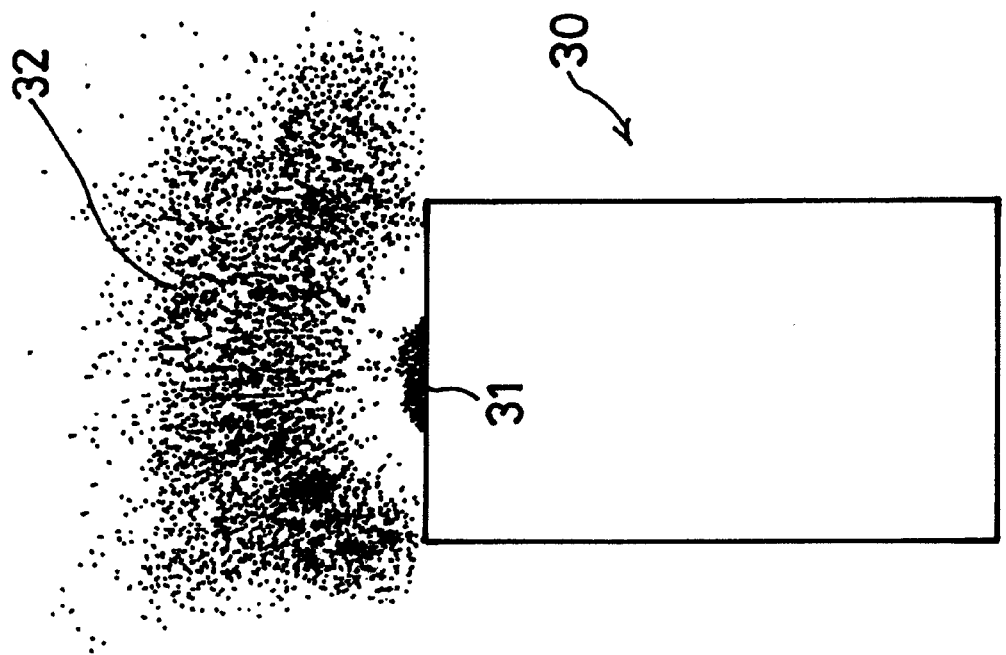
FIG. 4 shows a distribution of magnetic powder in a conventional magnet type medical instrument.
Figure 3:
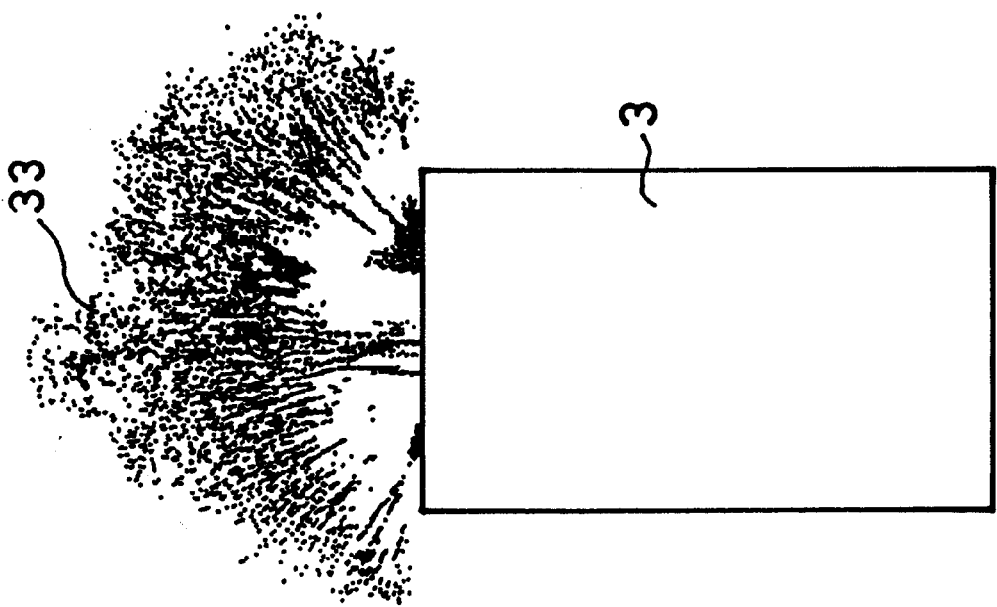
FIG. 3 shows a distribution of magnetic powder in the embodiment shown in FIG. 1.
Figure 5:
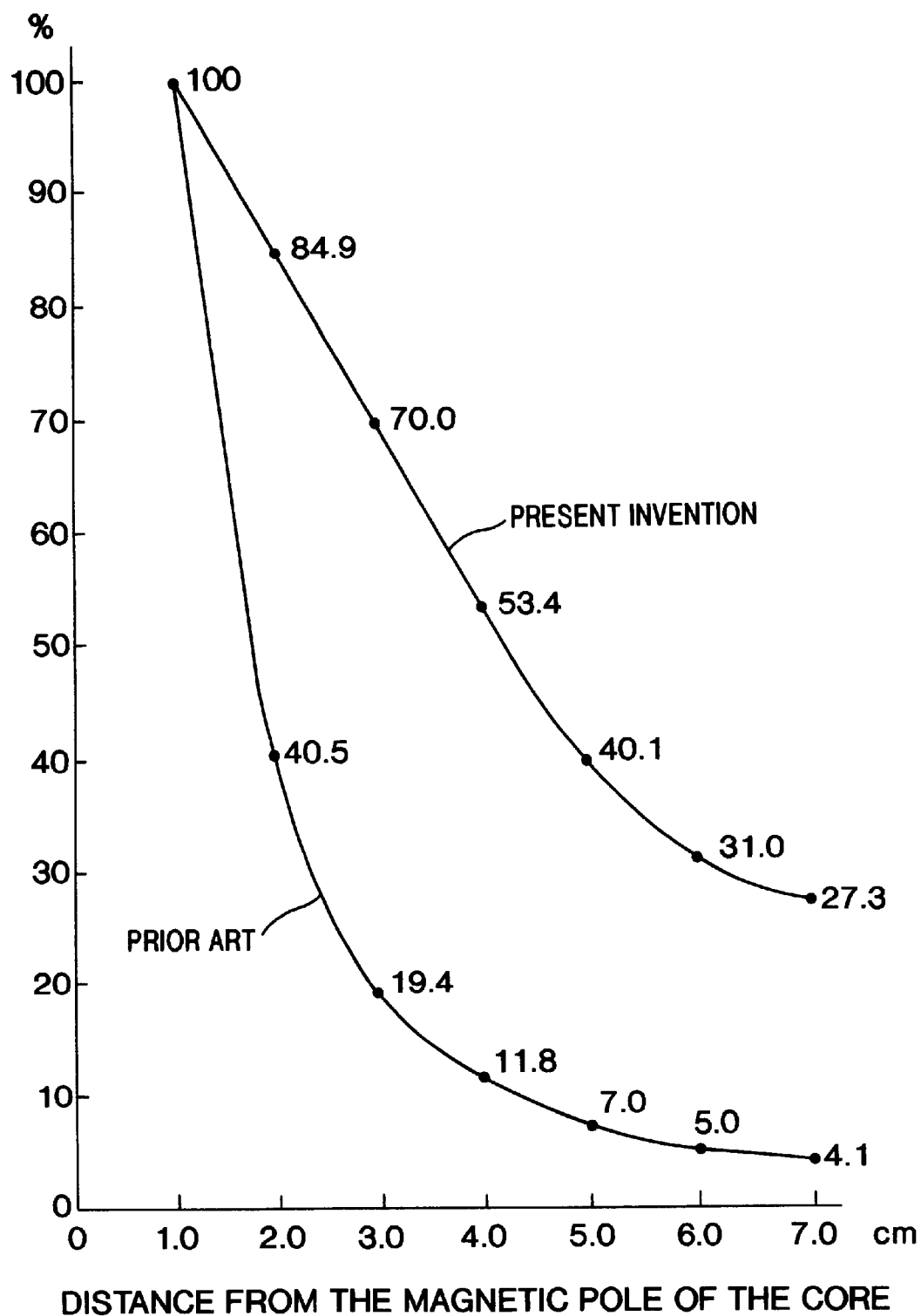
FIG. 5 shows curves representing the relation between the magnetic flux density and the distance from the magnetic pole of the core in comparison between the magnet type medical instrument according to the present invention and that of a conventional one.

FIG. 1 and FIG. 2 show an embodiment of an electromagnet in the magnet type medical instrument according to the present invention. A first core 1 which has a first inner space 2 is constituted by sheets of silicon steel or magnetic metal wound cylindrically. A first coil which has leads 3b, 3b to be connected to an electric source is wound round said first core 1 and generates a first magnetic field as shown in FIG. 3 by applying an alternating current, a commutated current or a pulsating current to said first coil.

Figure 6:
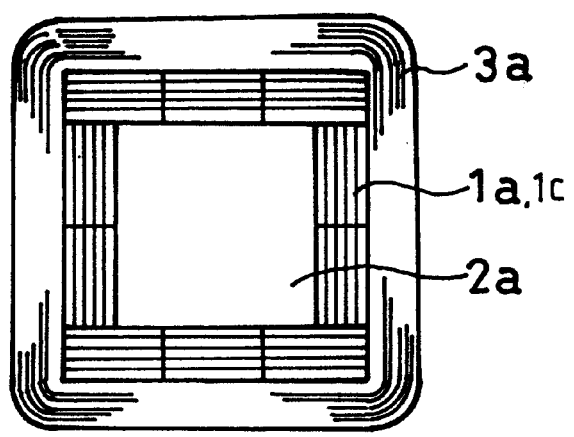
FIG. 6 shows a front view of another embodiment similar to the embodiment of an electromagnet and a coil in a magnet type medical instrument according to the present invention shown in FIG. 1.
Figure 7:
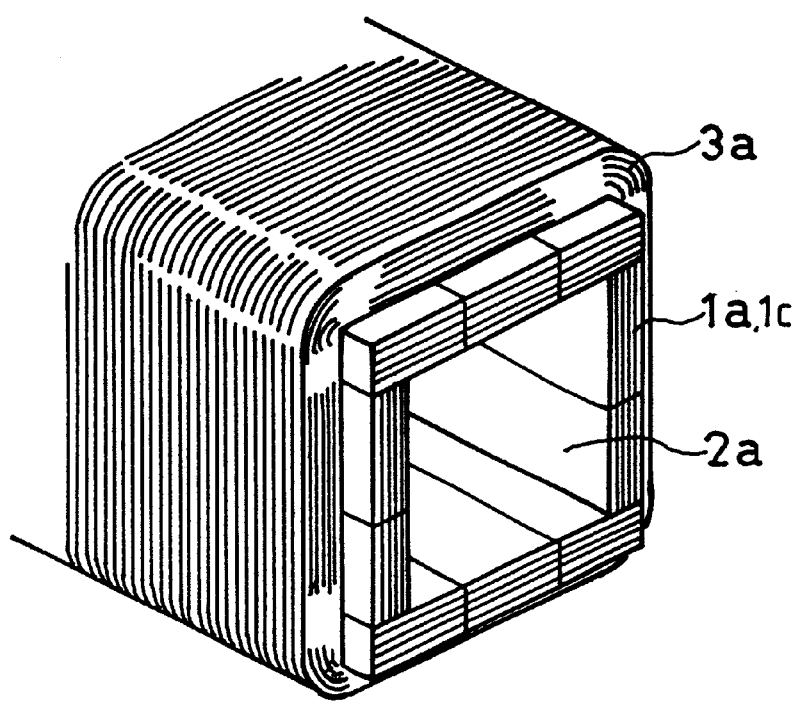
FIG. 7 shows a perspective view of the embodiment shown in FIG. 6.

FIG. 6 and FIG. 7 shows another embodiment of an electromagnet, similar to the embodiment shown in FIG. 1, in which a first core 1a is shaped in a shape like a square-sectioned sleeve and has a first inner space 2a.

In FIG. 1 and FIG. 2, a first core 1 shaped cylindrically may be replaced by a first bobbin 1b shaped cylindrically and made of non-magnetic metal. Likewise, in FIG. 6 and FIG. 7, a first core 1a shaped in a shape like a square-sectioned sleeve may be replaced by a first bobbin 1c made of nonmagnetic metal and shaped in a shape like a square-sectioned sleeve.

Figure 8:
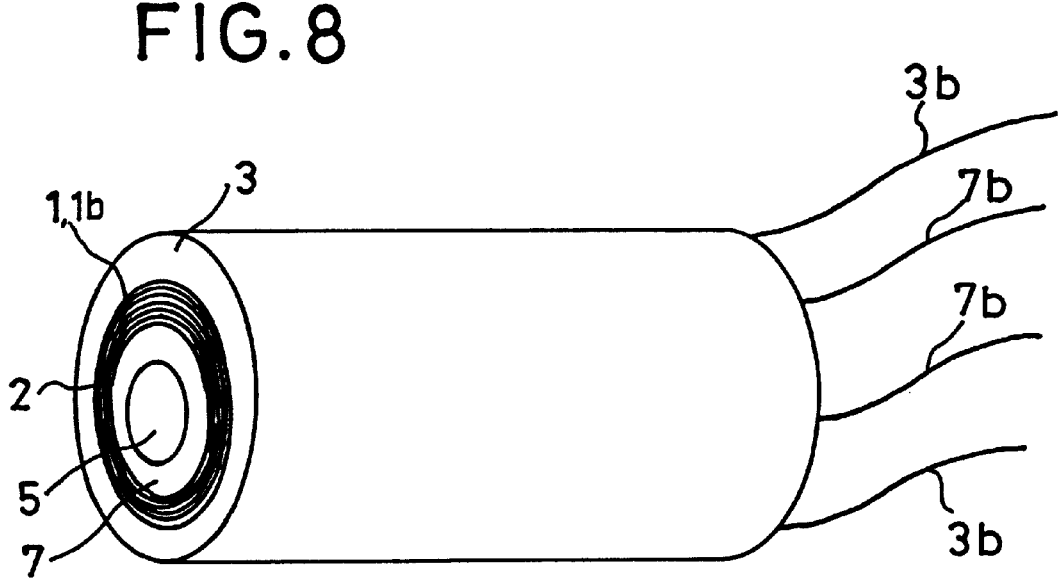
FIG. 8 shows a perspective view of another embodiment of an electromagnet and a coil in a magnet type medical instrument according to the present invention.
Figure 9:
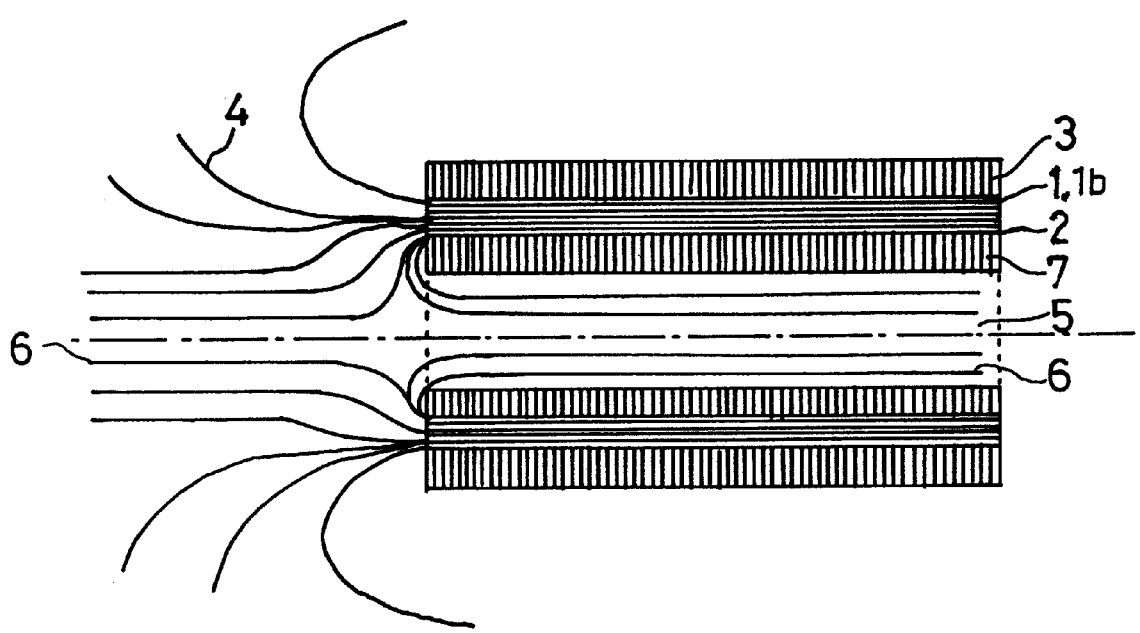
FIG. 9 shows a longitudinal section of the embodiment shown in FIG. 8.

FIG. 8 and FIG. 9 shows another embodiment of the magnet type medical instrument according to the present invention. It comprises a first core 1 and a first coil 3 with leads 3b, 3b as in an embodiment shown in FIG. 1 and in addition a second coil 7 which is wound in a first inner space 2 of said first core 1 so that it may form a second inner space 5 and which can generate a second magnetic field by applying an alternating current, a commutated current or a pulsating current to said second coil 7, said second coil 7 having leads 7b, 7b to be connected to an electric source. In this case, said first coil 3 and said second coil 7 are wound in the same direction so that the polarity of the first magnetic field 4 may coincide with that of the second magnetic field 6.

Furthermore, the number of turns of said first coil 3 and/or that of said second coil 7 can be regulated so that the phase of said first magnetic field 4 may coincide with that of said second magnetic field 6. The method of this regulation is as follows.

Figure 22:
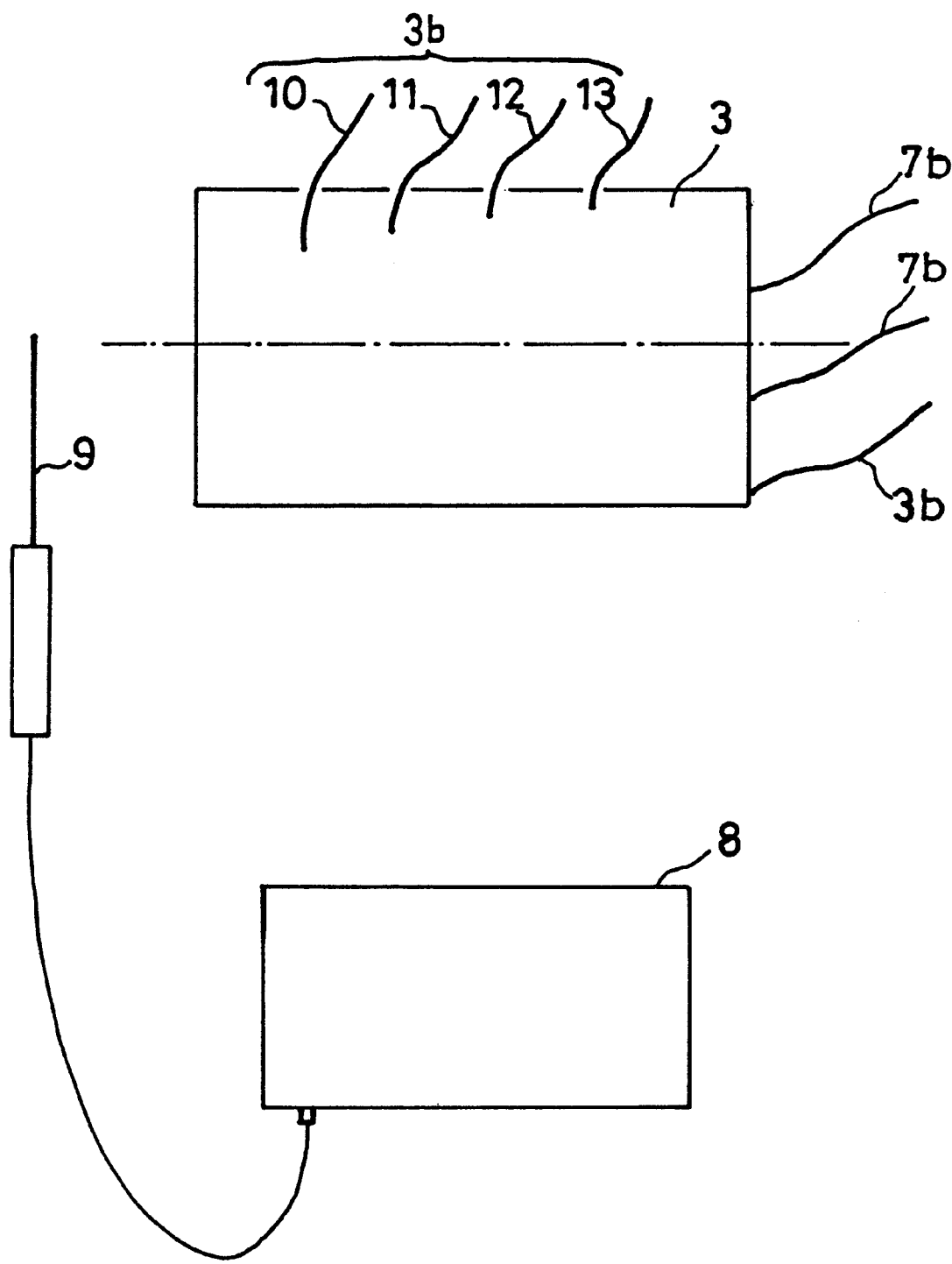
FIG. 22 shows a figure for explaining a process for the coincidence of the phase in case an alternating current, a commutated current or a pulsating current is applied to the coil in the embodiment shown in FIG. 8 to FIG. 16.

The probe 9 of a magnetic flux meter 8 shown in FIG. 22 is positioned at a point about 2 cm, for example, distant from a magnetic pole of said first core 1. The number of turns of said first coil 3 is 360 for example while that of said second coil 7 is 300. Intermediate electric terminals 10,11,12 and 13 are arranged at 240th, 270th, 300th and 330th points respectively of turns of said first coil 3. An alternating current or a pulsating current is applied to said first coil 3 and said second coil 7. Then said magnetic flux meter 8 chooses a point of the largest magnetic flux density of said four points 240th, 270th, 300th and 330th. In case this electromagnet is mass-produced, this chosen point is adopted for the regular lead 3b.

Figure 20:
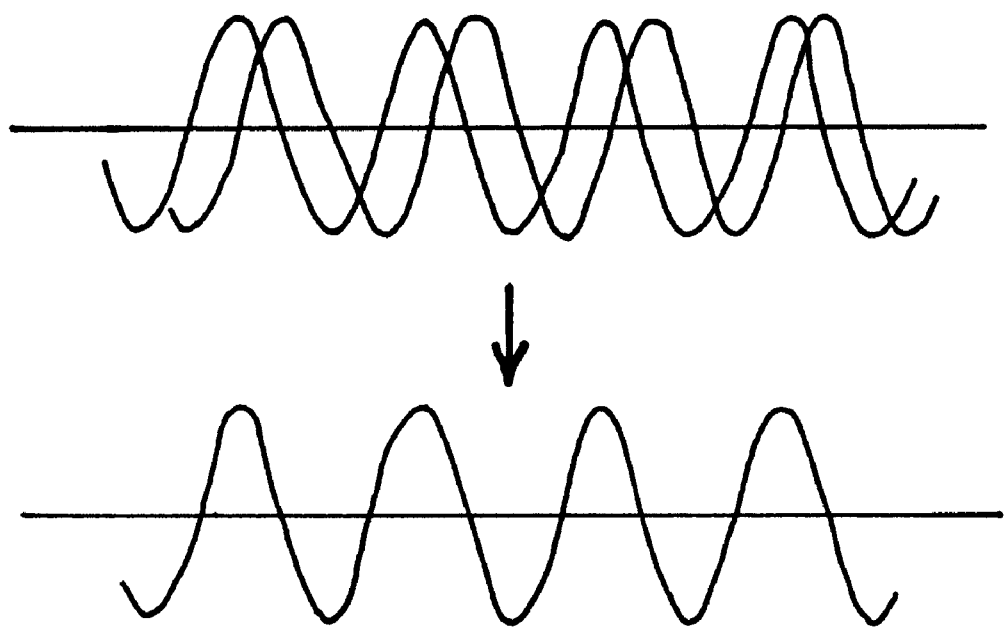
FIG. 20 shows curves for explaining the coincidence of the phase in case an alternating current is applied to the coil in the embodiments shown in FIG. 8 to FIG. 16.
Figure 21:
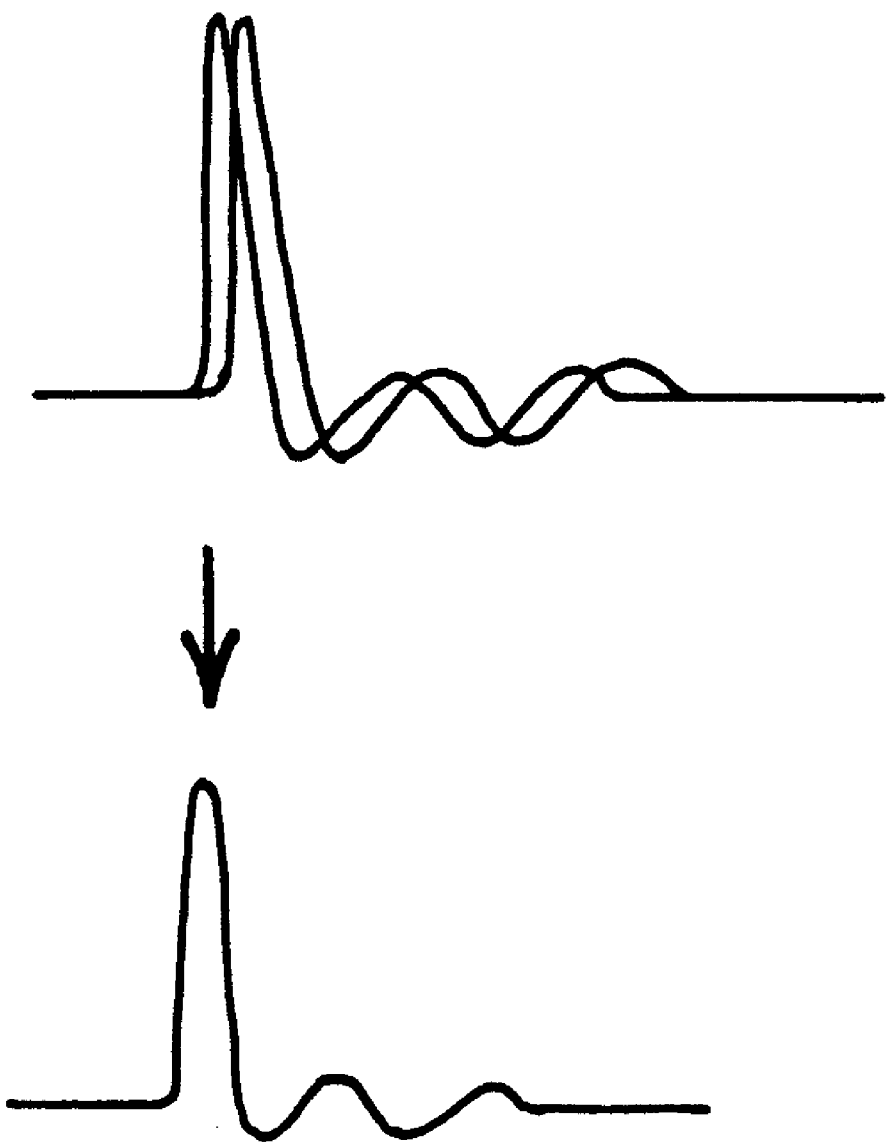
FIG. 21 shows curves for explaining the coincidence of the phase in case a pulsating current is applied to the coil in the embodiments shown in FIG. 8 to FIG. 16.

FIG. 20 shows current-time curves in a case in which an alternating current is applied to said first and second coils while FIG. 21 shows current-time curves in a case in which a pulsating current is applied to the coils. In both the cases the upper two curves show a case in which there is no coincidence of the phase between them before regulation while the lower single curve shows a case in which there is a coincidence of the phase between them after regulation.

The lower curve means that one of said four points is chosen as mentioned above as a result of the regulation. There is not only a case in which the number of turns of said first coil 3 only is regulated but also there is a case in which the number of turns of said second coil 7 only or the numbers of turns of both said first coil 3 and said second coil 7 is/are regulated.

Figure 10:
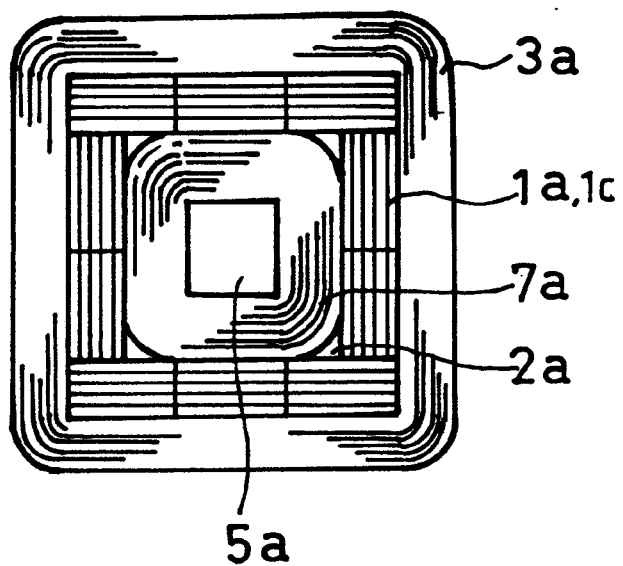
FIG. 10 shows a front view of another embodiment similar to the embodiment shown in FIG. 8.
Figure 11:
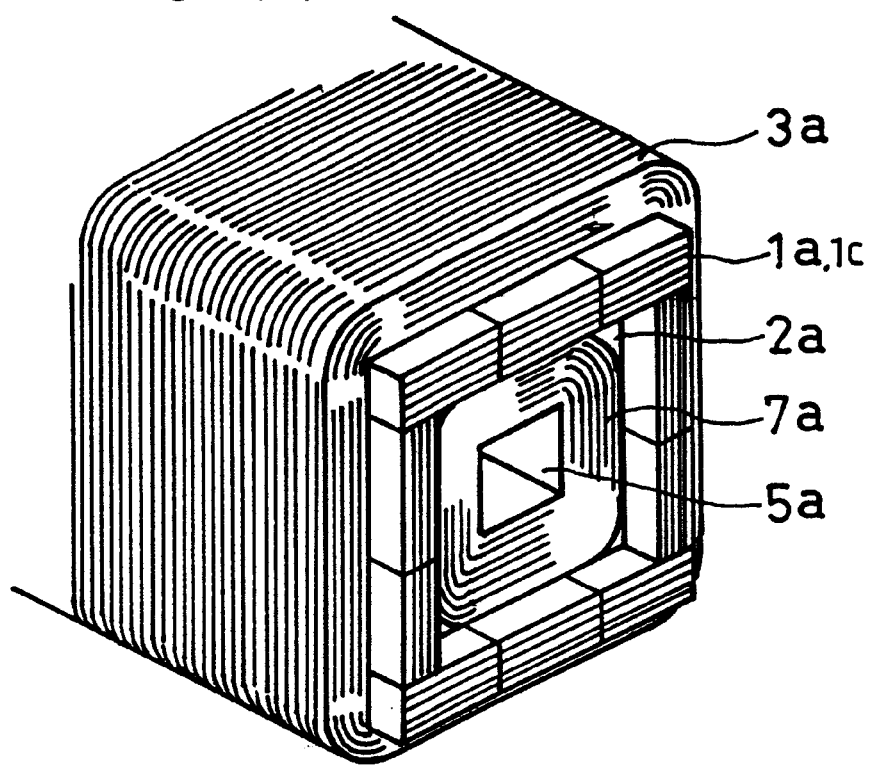
FIG. 11 shows a perspective view of the embodiment shown in FIG. 10.

FIG. 10 and FIG. 11 show another embodiment of the magnet type medical instrument similar to the embodiment shown in FIG. 8. In this case, a first core 1a, round which a first coil 3a is wound, is shaped in a shape like a square-sectioned sleeve and has a first inner space 2a in which a second coil 7a is wound with a second inner space 5a inside.

In an embodiment shown in FIG. 8 and FIG. 9, a cylindrical first core 1 may be replaced by a cylindrical first bobbin 1b made of non-magnetic material. Likewise, in an embodiment shown in FIG. 10 and FIG. 11, a first core 1a shaped in a shape like a square-sectioned sleeve may be replaced by non-magnetic first bobbin 1c shaped in the same shape.

Figure 12:
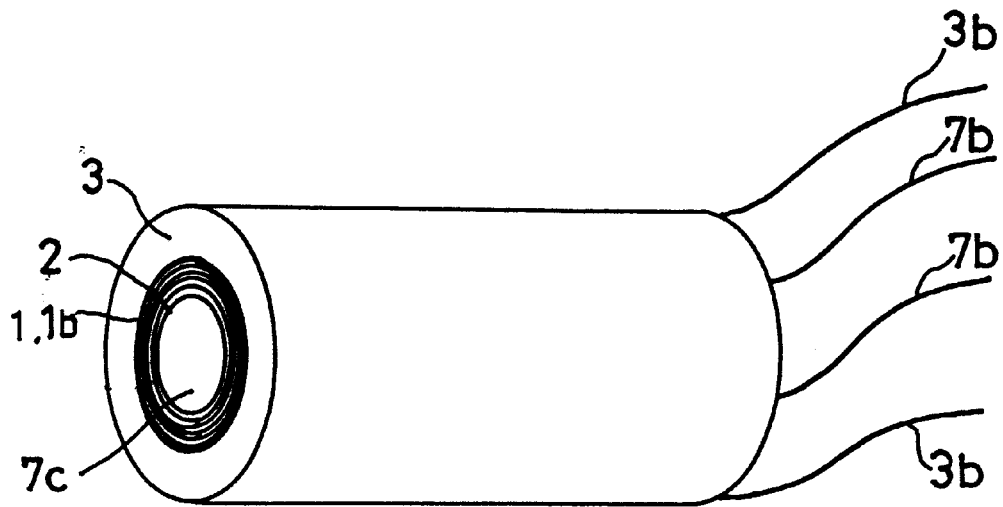
FIG. 12 shows a perspective view of another embodiment of an electromagnet and a coil in the magnet type medical instrument according to the present invention.

FIG. 12 shows another embodiment of an electromagnet of the magnet type medical instrument according to the present invention. This electromagnet has parts common to those of the electromagnet shown in FIG. 8. However there is a definitely different point between them. That is to say, a second coil 7c shown in FIG. 12 is wound to its axis without forming a second inner space 5 in the first inner space 2 of the first core 1 while a second coil 7 shown in FIG. 8 is wound with a second inner space 5 in the second inner space 2 of the first core 1.

Figure 14:
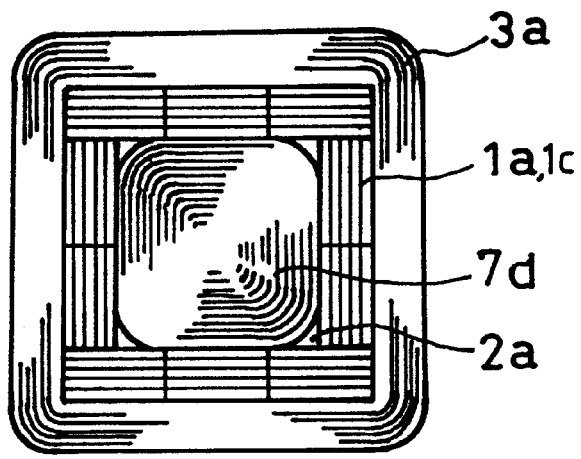
FIG. 14 shows a front view of another embodiment similar to the embodiment of an electromagnet and a coil in the magnet type medical instrument shown in FIG. 12.
Figure 15:
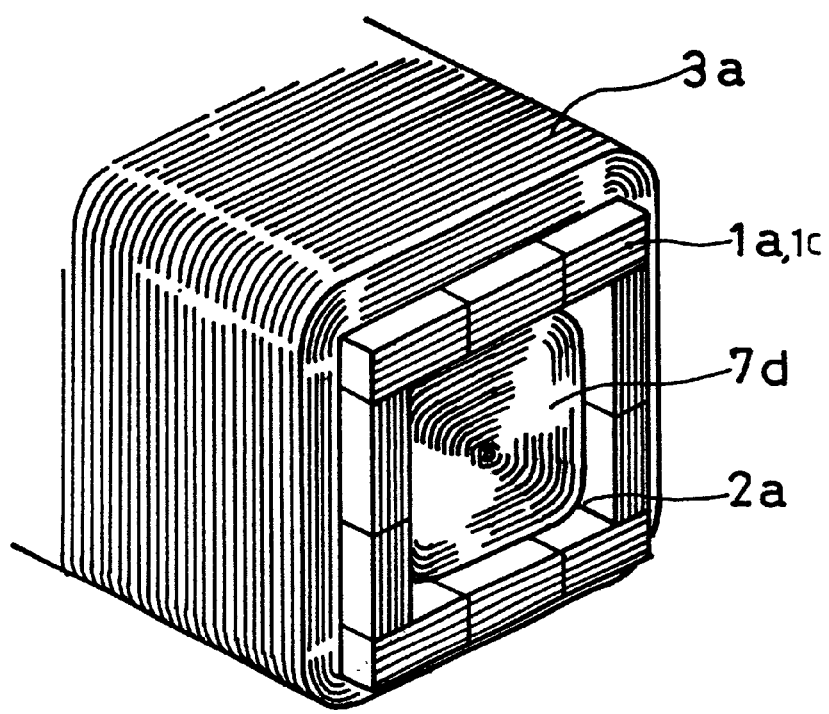
FIG. 15 shows a perspective view of the embodiment shown in FIG. 14.

FIG. 14 and FIG. 15 show another embodiment similar to the embodiment shown in FIG. 12. This electromagnet, round which a first coil 3a is wound, is shaped in a shaped like a square-sectioned sleeve and has a first inner space 2a in which a second coil 7d is wound to its axis without forming a second inner space 5a inside.

Figure 13:
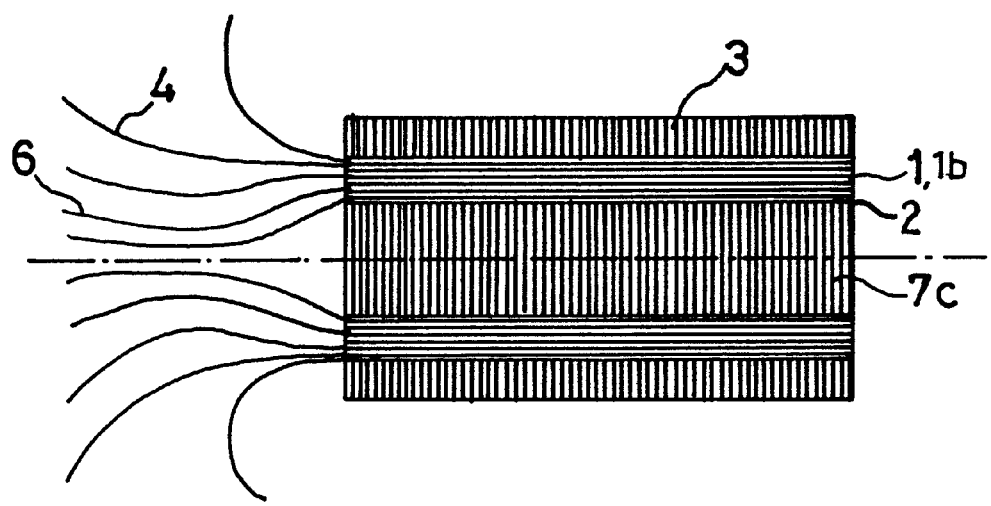
FIG. 13 shows a longitudinal section of the embodiment shown in FIG. 12.

In an embodiment shown in FIG. 12 and FIG. 13, a cylindrical first core 1 may be replaced by a cylindrical first bobbin 1b made of non-magnetic material. Likewise, in an embodiment shown in FIG. 14 and FIG. 15, a square type first core 1a may be replaced by a square type first bobbin 1c made of non-magnetic material.

Figure 16:
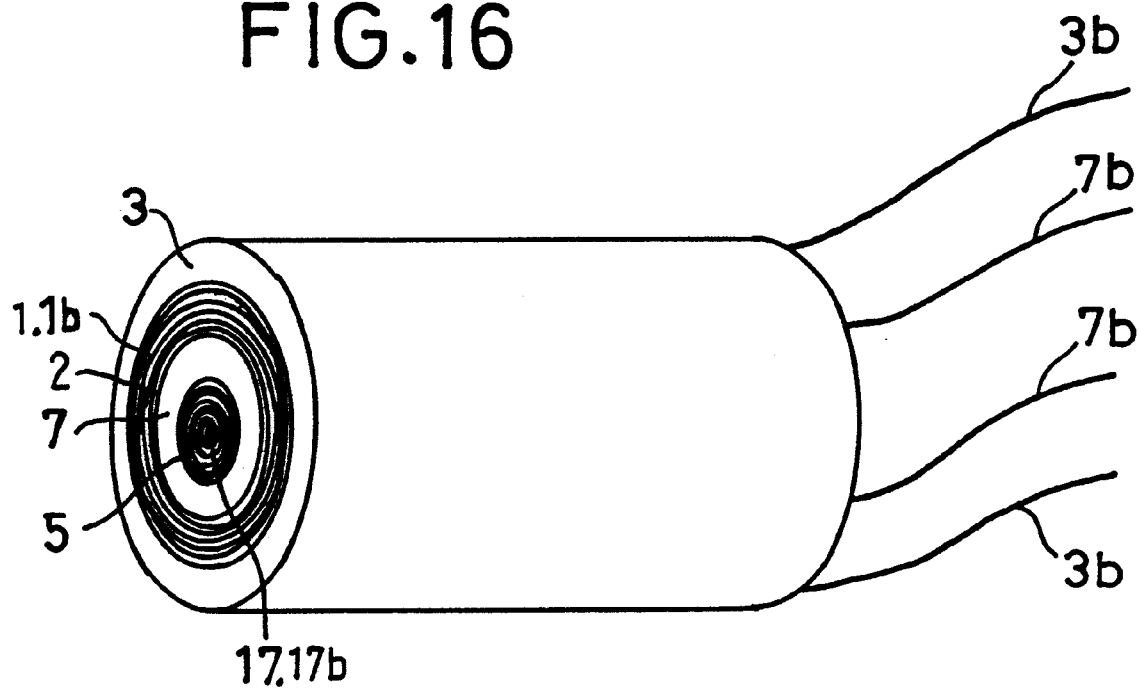
FIG. 16 shows a perspective view of another embodiment of an electromagnet and a coil in the magnet type medical instrument according to the present invention.
Figure 17:
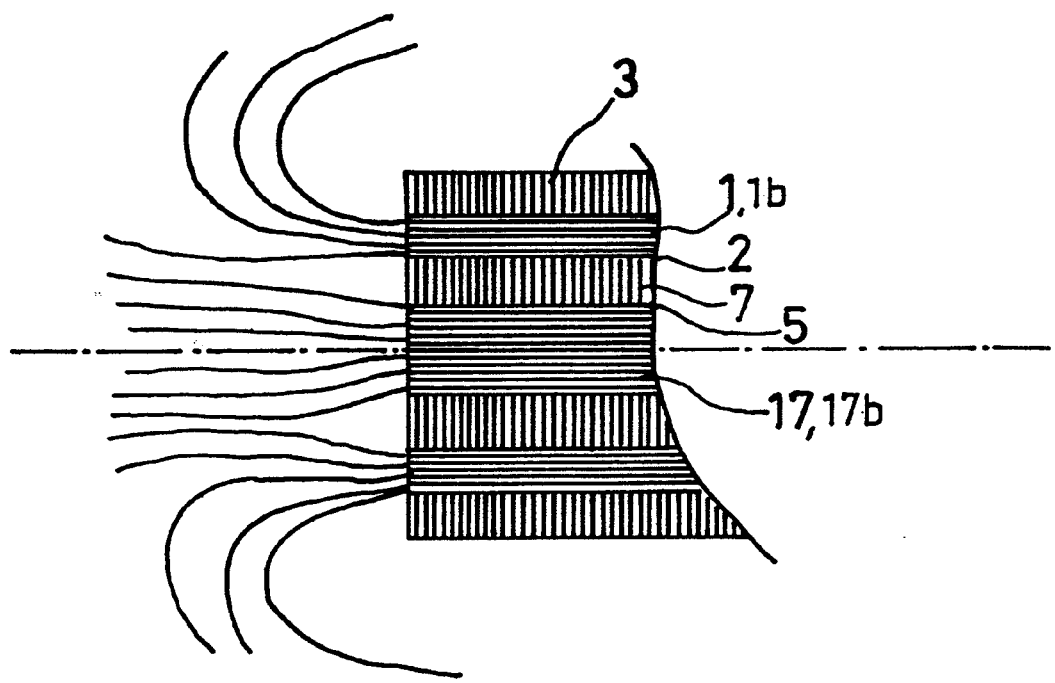
FIG. 17 shows a partial longitudinal section of the embodiment shown in FIG. 16.

FIG. 16 and FIG. 17 show another embodiment of a electromagnet in the magnet type medical instrument according to the present invention. This electromagnet has a second core 17 in its second inner space 5, said second core 17 being excluded in an embodiment shown in FIG. 8.

Figure 18:
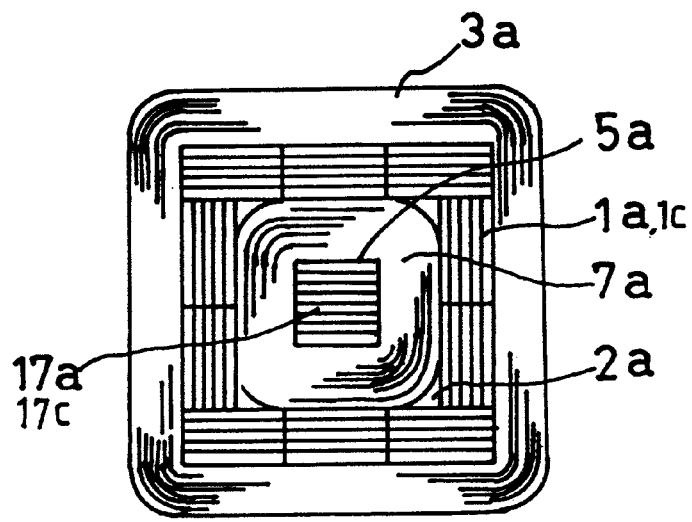
FIG. 18 shows a front view of another embodiment similar to the embodiment of an electromagnet and a coil in the magnet type medical instrument shown in FIG. 16.
Figure 19:
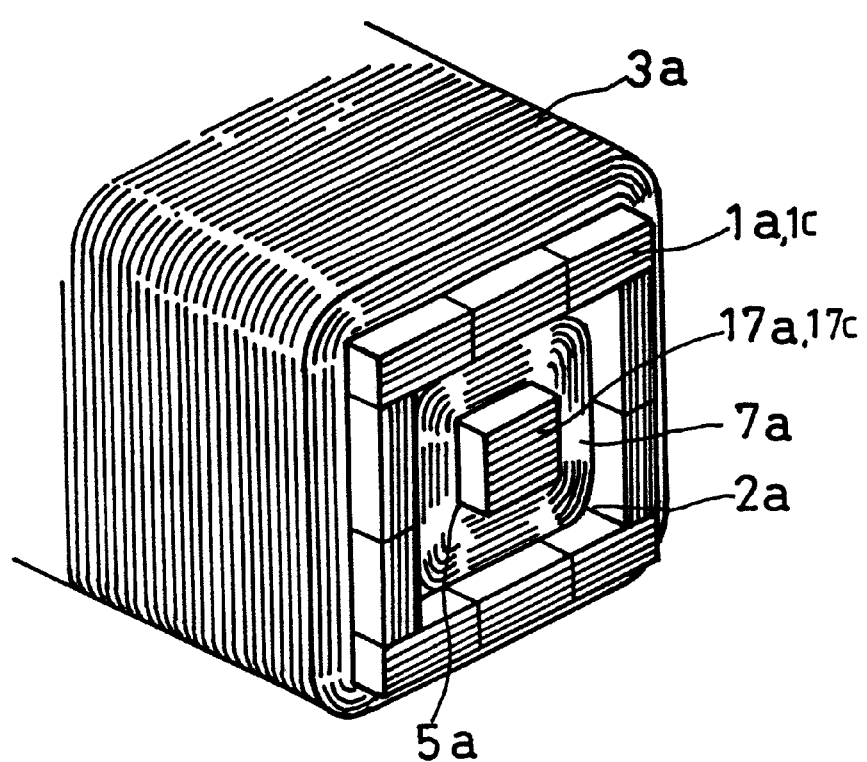
FIG. 19 shows a perspective view of the embodiment shown in FIG. 18.

FIG. 18 and FIG. 19 show another embodiment similar to the embodiment shown in FIG. 16. A first core 1a, round which a first coil 3a is wound, is shaped in a shape like a square-sectioned sleeve and has a first inner space 2a in which a second coil 7a is wound. A second core 17a is arranged in this second coil 7a.

In the embodiment shown in FIG. 16 and FIG. 17, a cylindrical first core 1 may be replaced by a cylindrical first bobbin 1b made of non-magnetic material and a second core 17 may be replaced by a second bobbin 17b made of nonmagnetic material.

Likewise in the embodiment shown in FIG. 18 and FIG. 19, a square type first core 1a may be replaced by a square type first bobbin 1c made of non-magnetic material and a second core 17a may be replaced by a second bobbin 17c made of non-magnetic material.

Figure 23:
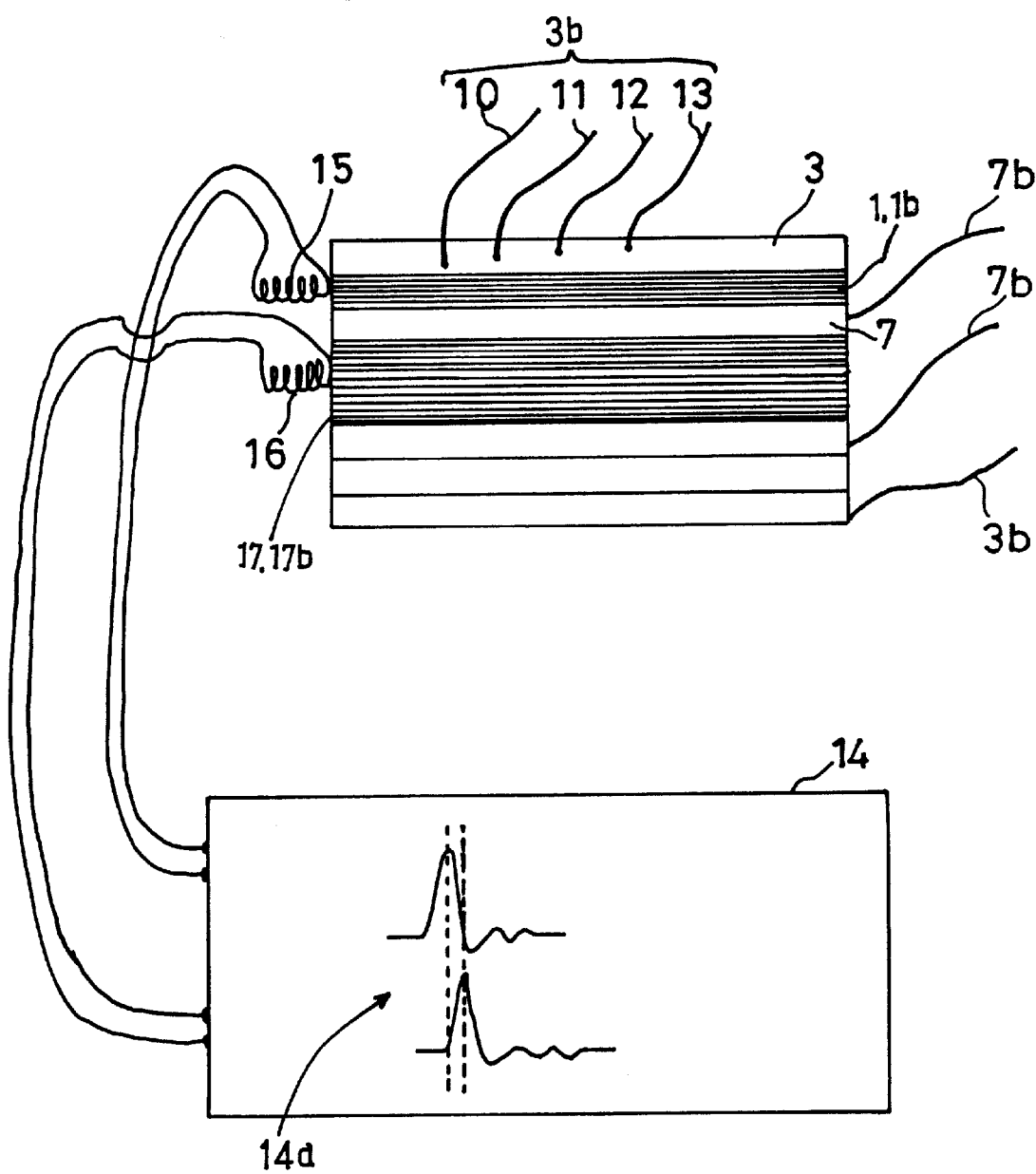
FIG. 23 shows a figure for explaining another process for the coincidence of the phase in case an alternating current, a commutated current or a pulsating current is applied to the coil in the embodiment shown in FIG. 8 to FIG. 16.

An embodiment of a magnet type medical instrument shown in FIG. 23 comprises an oscilloscope 14. Sensors 15,16 attached to it are constituted by coils 15,16 respectively of five turns for example which are stuck to the magnetic poles of a first core 1 and a second core 17 respectively. As the oscilloscope 14 displays two current curves 14a corresponding to the number of turns of the coil, one of the electric terminals 10,11,12 and 13 of the first coil 3 is chosen on condition that the phase of the current of the upper curve shown in FIG. 23 coincides with that of the lower curve shown in FIG. 23. In case the electromagnet is mass-produced, this chosen one is adopted for the regular lead 3b.

FIG. 20 and FIG. 21 show current-time curves in case an alternating current and a pulsating current respectively are applied to the coils. By choice of one of the electric terminals 10,11,12 and 13, curves of different phases as shown in upper figures can be replaced by curves of same phases as shown in lower figures.

There is not only a case in which the number of turns of a first coil 3 only is regulated but also there is a case in which the number of turns of a second coil 7 only or the numbers of turns of both a first coil 3 and a second coil 7 is/are regulated.

The phases of currents for the embodiments shown in FIG. 8 to FIG. 19 can be made coincident by using a magnetic flux meter 8 shown in FIG. 22 and those for the embodiments shown in FIG. 16 to FIG. 19 except FIG. 8 to FIG. 15 can be made coincident by using an oscilloscope 14 shown in FIG. 23.

Figure 24:
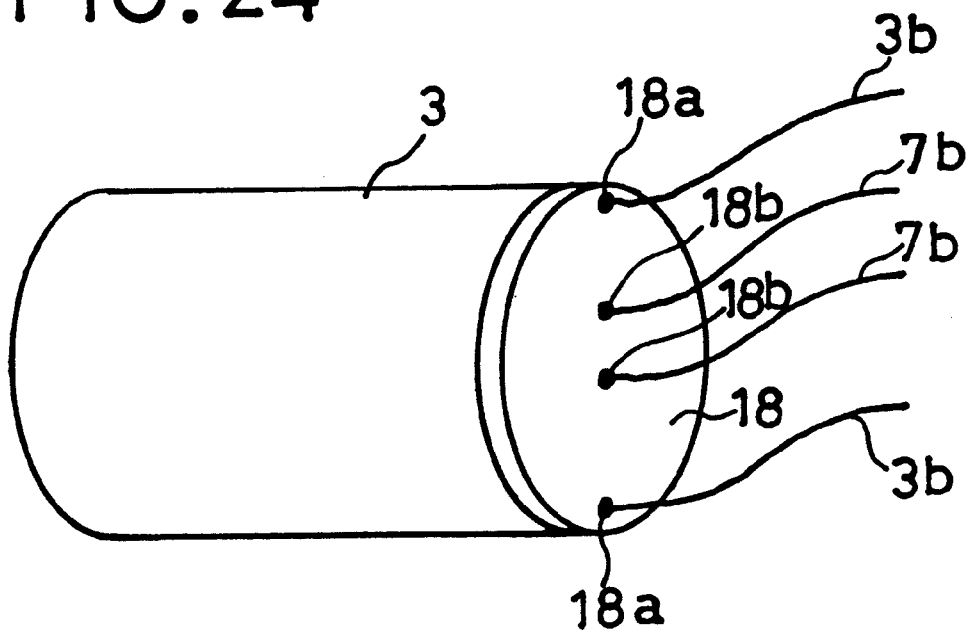
FIG. 24 shows a perspective view of an embodiment similar to the embodiment of an electromagnet and a coil in the magnet type medical instrument shown in FIG. 12 with a disk-like yoke stuck to an end of each of them.
Figure 25:
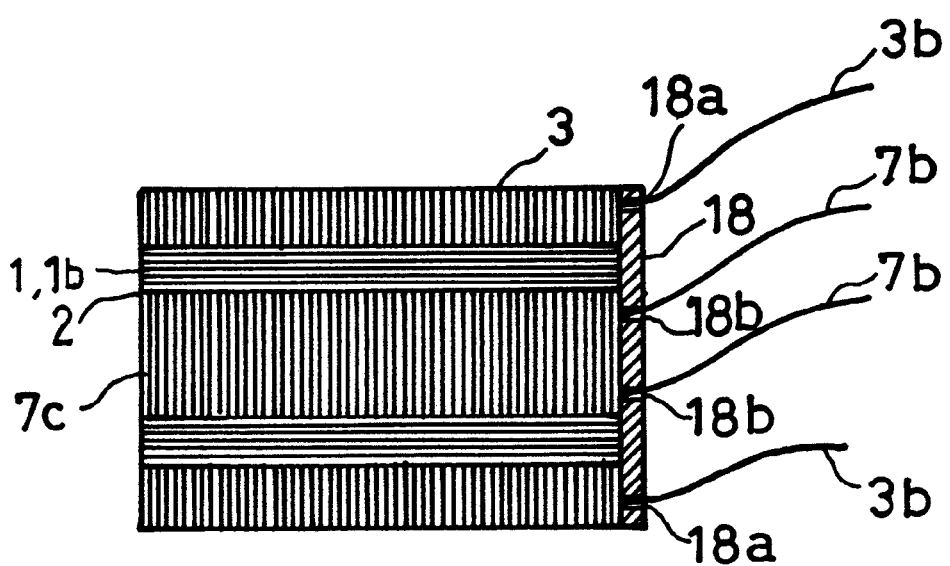
FIG. 25 shows a longitudinal section of the embodiment shown in FIG. 24.

FIG. 24 and FIG. 25 show another embodiment of the electromagnet in the magnet type medical instrument according to the present invention. In this case, a disk-like yoke 18 as described below is added to the embodiment shown in FIG. 12.

The disk-like yoke 18 is stuck to an end of each of a first core 1 and first and second coils 3, 7c by adhesive so as to enclose them. Two leads 3b, 3b of a first coil 3 pass through two holes 18a, 18a of said disk-like yoke 18 and two leads 7b, 7b of a second coil 7 pass through two holes 18b, 18b of said yoke 18, all the leads 3b, 3b, 7b, 7b being connected to an electric source not shown. The leads 3b, 3b of said first coil 3, the leads 7b, 7b of said second coil 7 and said disk-like yoke 18 are insulated electrically at the holes 18a, 18a 18b, 18b.

In the embodiment shown in FIG. 24 and FIG. 25, a cylindrical first core 1 may be replaced by a cylindrical first bobbin 1b made of non-magnetic material.

The disk-like yoke 18 may be also applied to any other embodiment than that shown in FIG. 12.

Then we explain a magnet type medical instrument shown in FIG. 26 below.

In a transformer 20, a primary voltage from an alternating current source 21 is applied to a primary winding 22 and transformed into a secondary voltage at a secondary winding 23 as an output voltage.

A human body 25 is put between a pair of electromagnets 24, 24 of the magnet type medical instrument which generate a magnetic field by said secondary voltage from said secondary winding 23.

A pair of supporting elements 26, 26 support a pair of electromagnets 24,24 of the magnet type medical instrument.

A fixing bed can slide the pair of supporting elements 26, 26 so as to make them move close to or apart from each other so that the electromagnets 24, 24 and the human body 25 may be made to move close to or apart from each other.

A pair of sliding terminals 28, 28 are attached to a pair of supporting elements 26, 26, slide in contact with the secondary winding 23 so as to regulate the number of turns of it corresponding to the distance between the pair of electromagnets 24, 24 for medical use and the human body 25 and apply the secondary voltage transformed from the primary one to the electromagnets 24,24.

In this case, it is proper to put a current commutation or conversion device 29 which can commutate an alternating current or convert the latter into a pulsating current, between the pair of slide terminal 28, 28 and the pair of the electromagnets 24, 24 for medical use.

Figure 27:
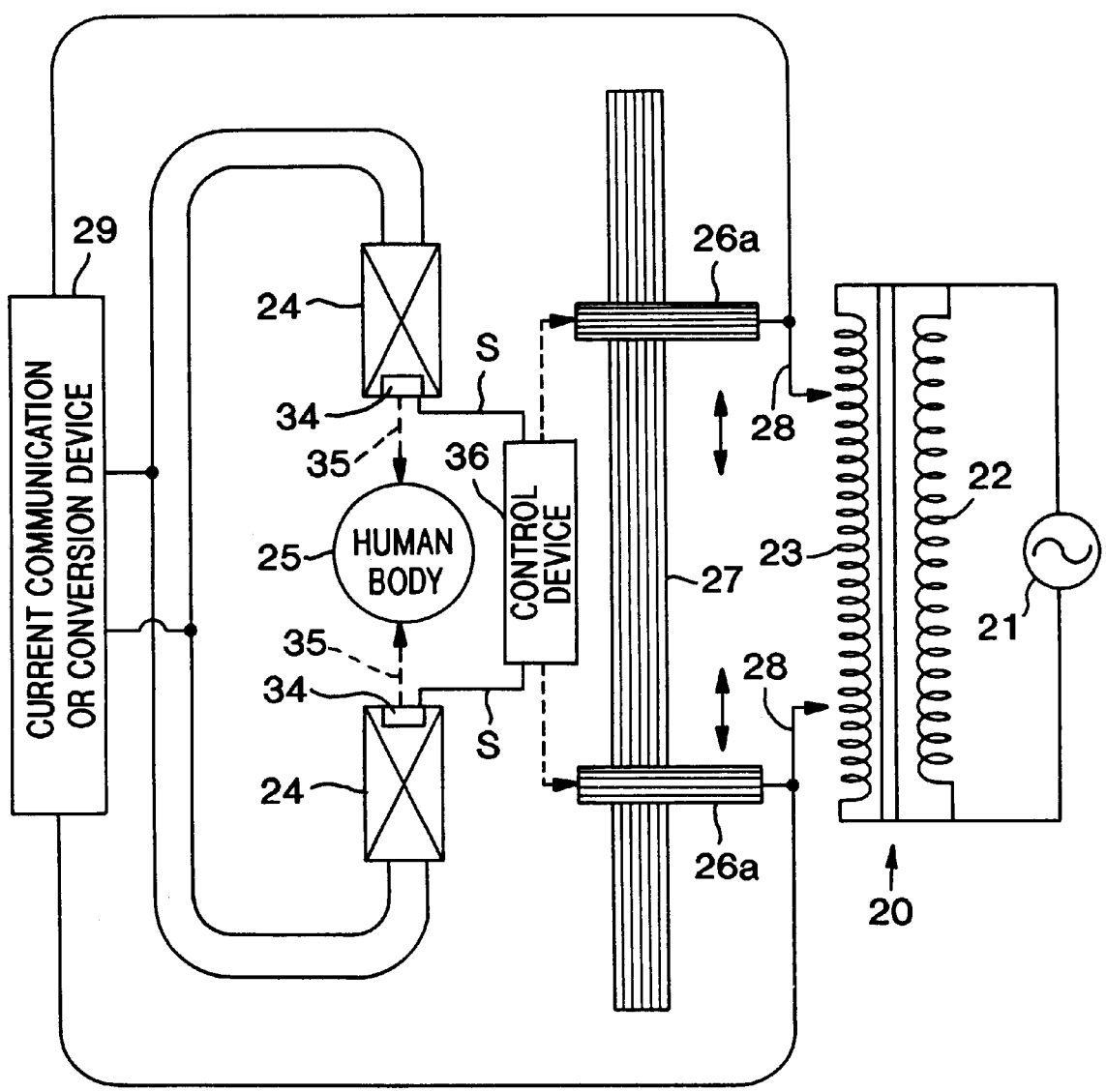
FIG. 27 shows a diagram for explaining the constitution of another embodiment of the magnet type medical instrument according to the present invention.

Then we explain another embodiment of the magnet type medical instrument according to the present invention shown in FIG. 27.

In a transformer 20 the primary voltage from an alternating current source 21 is applied to a primary winding 22 and transformed into a secondary voltage at a secondary winding 23 as an output voltage.

A human body 25 is put between a pair of the electromagnets 24, 24 of the magnet type medical instrument which generate a magnetic field by secondary voltage from the secondary winding 23.

A pair of distance sensors 34, 34 are attached to the electromagnets 24, 24 for medical use, emit infrared rays 35, 35 against the human body 25 and detect the distance from the latter by receiving the infrared rays reflected from it.

A pair of sliding terminals 28, 28 are attached to a pair of supporting elements 26a, 26a and slide in contact with a secondary winding 23 so as to change the number of turns of the latter thereby to apply the secondary voltage transformed to the pair of electromagnets 24, 24 for medical use.

A fixing bed 27 can slide the pair of supporting elements 26a, 26a to make them move close to or apart from each other.

A control device 36 has a driving mechanism which can control the distance between the pair of the supporting elements 26a, 26a so as to change the distance between the pair of the slide terminals 28, 28 corresponding to a signal S received from the pair of the distance sensors 34, 34 corresponding to the distance between the pain of the electromagnets 24, 24 for medical use and the human body 25. The driving mechanism comprises a motor and gears which are controlled by a microcomputer put in the control device 36.

In this case, it is proper to put a current commutation or conversion device 29 which can commutate an alternating current or convert the latter into a pulsating current, between the pair of the slide terminals 26, 26 and the electromagnets 24, 24 for medical use.

Figure 26:
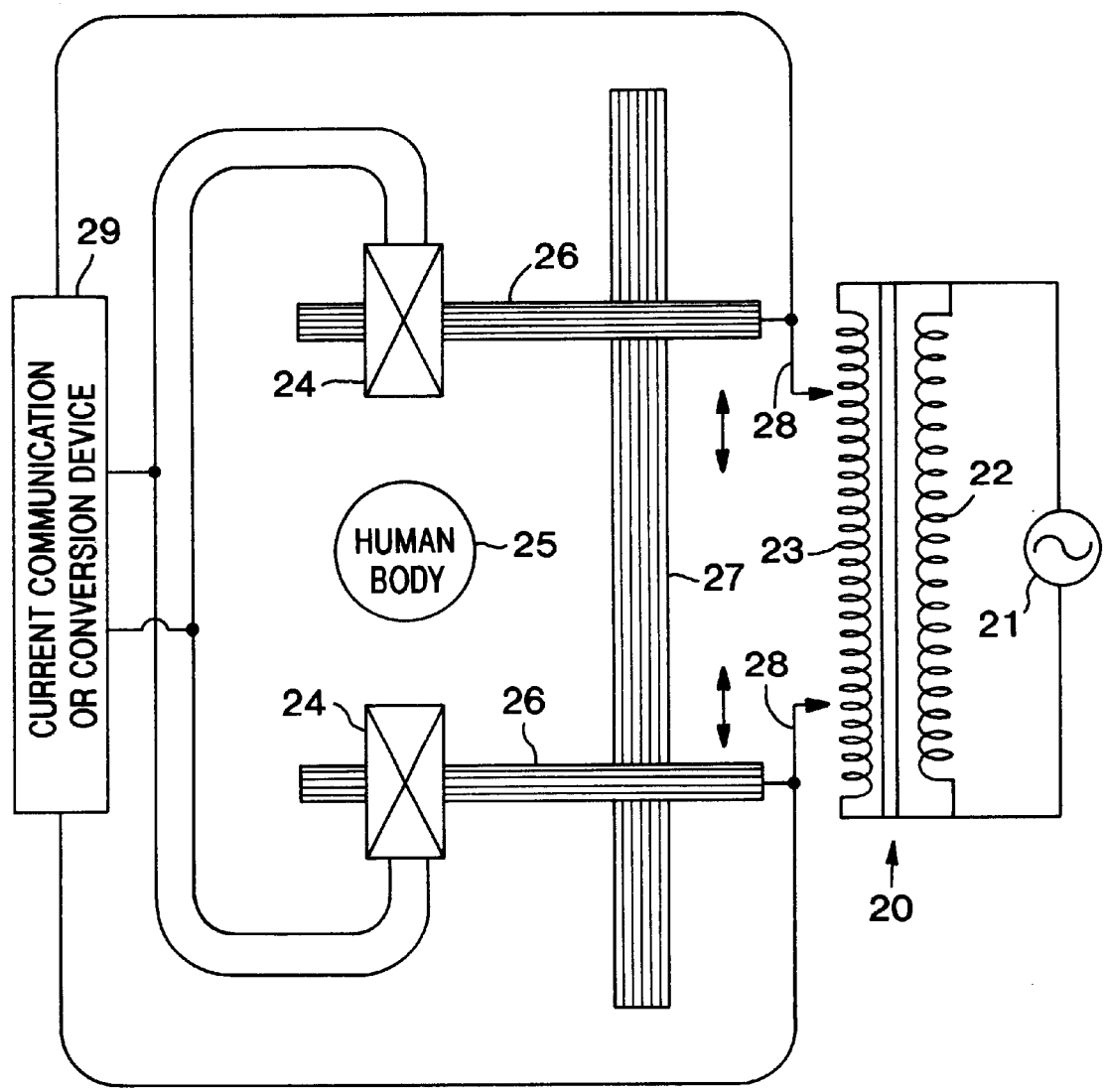
FIG. 26 shows a diagram for explaining the constitution of an embodiment of the magnet type medical instrument according to the present invention.

In the embodiments shown in FIG. 26 and FIG. 27, the pair of the electromagnets 24, 24 for medical use may be the conventional type electromagnets constituted by a core and a coil wound round the core or may be the electromagnets shown in FIG. 1, FIG. 2, FIG. 6 to FIG. 19, FIG. 24 and FIG. 25.

In the embodiments shown in FIG. 26 and FIG. 27, a pair of electromagnets for medical use may be replaced by a pair of coils for medical use shown in FIG. 2, FIG. 6 to FIG. 19, FIG. 24 and FIG. 25.

Figure 28:
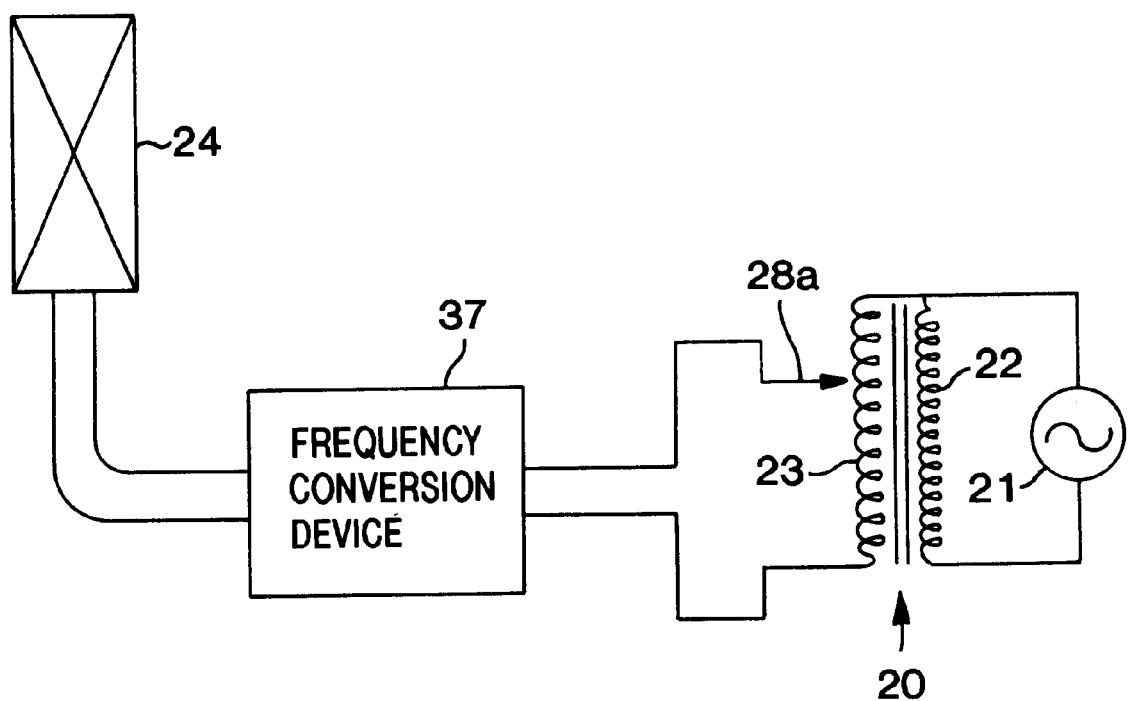
FIG. 28 shows a diagram for explaining the constitution of another embodiment of the magnet type medical instrument according to the present invention.

Then we explain another embodiment of the magnet type medical instrument according to the present invention shown in FIG. 28.

This instrument comprises an electromagnet 24 or a pair of electromagnets 24 for medical use, a transformer 20 for applying a transformed alternating current to the electromagnet 24 and a frequency conversion device 37 which is used to convert the frequency of the transformed alternating current into 5 to 40 Hz and which is arranged between the electromagnet 24 and the transformer 20. In the transformer 20, a primary alternating current from an alternating current source 21 is applied to the primary winding 22 and transformed secondary current is transmitted from the secondary winding 23 via the terminal 28a and the frequency conversion device 37 to the electromagnet 24.

In the embodiment shown in FIG. 28, a pair of the electromagnets 24 may be a pair of a conventional type electromagnets consisting of a core and a coil wound round the core or may be a pair of the electromagnets shown in FIG. 1, FIG. 2, FIG. 6 to FIG. 19, FIG. 24 and FIG. 25.

In the embodiment shown in FIG. 28, a pair of electromagnets may be replaced by a pair of coils for medical use shown in FIG. 2, FIG. 6 to FIG. 19, FIG. 24 and FIG. 25.

What is claimed is:

1. An electromagnet for a magnetic medical instrument comprising a cylindrical first core with a first inner space and a first coil wound around said first core, said electromagnet adapted to generate a first magnetic field by applying an alternating current, a commutated current, or a pulsating current to said first coil, a second coil, wound around a second core in said first inner space to form a second inner space, adapted to generate a second magnetic field by applying said alternating current or said pulsating current to said second coil, said first coil and said second coil wound in a same direction so that a polarity of said first magnetic field coincides with that of said second magnetic field, and a number of turns of at least one of said first coil and said second coil is regulated so that a phase of said first magnetic field coincides with that of said second magnetic field.

2. The electromagnet of claim 1 wherein said second coil is wound around said second core without forming said second inner space in said first inner space of said first core.

3. The electromagnet of claim 1 wherein said second core is in said second inner space.

4. The electromagnet of claim 1 comprising a yoke contacting an end of said first core or an end of each of said first core and a second core to enclose said end.

5. The electromagnet of claim 4 wherein said yoke is a disc.

6. The electromagnet of claim 1 wherein said first core or said first core and a second core comprise steel sheets wound in a circular- or square-sectioned sleeve.

7. A magnetic medical instrument comprising a transformer having a primary winding adapted to receive a primary voltage from a source of alternating current, and a secondary winding adjacent said primary winding adapted to convert said primary voltage into an output voltage;

a pair of electromagnets which generates a magnetic field by application of said output voltage to said electromagnets whereby pain in at least a portion of a human body between said electromagnets is ameliorated;

a pair of supporting elements for said electromagnets, a fixing bed for moving said electromagnets toward and away from each other, whereby said electromagnets move close to and away from said human body; and a pair of sliding terminals, attached to said supporting elements, which slide axially in contact with said secondary winding, thereby regulating a number of active turns of said secondary winding based on a distance between said pair of electromagnets and said human body, whereby said output voltage applied to said electromagnets is varied.

8. The magnetic medical instrument of claim 7 comprising a device adapted to commutate or convert said alternating current into a pulsating current, said device located between said sliding terminals and said pair of electromagnets.

9. The magnetic medical instrument of claim 7 wherein each of said pair of electromagnets comprises a core and a coil wound around said core.

10. A magnetic medical instrument comprising a transformer having a primary winding adapted to receive a primary voltage from a source of alternating current, and a secondary winding adjacent said primary winding adapted to convert said primary voltage into an output voltage;

a pair of electromagnets which generate a magnetic field by application of said output voltage to said electromagnets whereby pain in at least a portion of a human body between said electromagnets is ameliorated;

a pair of distance sensors, attached to said pair of electromagnets, applying infrared rays against said human body and detecting a distance between said pair of electromagnets and said human body by receiving said infrared rays reflected from said human body, a pair of supporting elements for said electromagnets, a fixing bed for moving said pair of supporting elements close to or apart from each other;

a pair of sliding terminals, attached to said pair of supporting elements, which slide axially in contact with said secondary winding, thereby regulating a number of active turns of said secondary winding, whereby said output voltage applied to said electromagnets is varied;

a control device including a driving mechanism for changing a distance between said supporting elements, which also changes a distance between said sliding terminals based on an input signal from said pair of distance sensors corresponding to a distance between said pair of electromagnets and said human body.

11. The magnetic medical instrument of claim 9 comprising a device adapted to commutate or convert said alternating current into a pulsating current, said device located between said sliding terminals and said pair of electromagnets.

* * * * *